United States Patent [19]

Kessler et al.

[11] Patent Number: 5,552,598
[45] Date of Patent: Sep. 3, 1996

[54] DETERMINATION OF DOWNHOLE FLOW REGIME IN A HORIZONTAL WELLBORE BY USING CENTER SAMPLE AND FULLBORE GAS-LIQUID HOLDUP MEASUREMENTS

[75] Inventors: Calvin W. Kessler; Gary J. Frisch, both of Houston, Tex.

[73] Assignee: Halliburton Company, Houston, Tex.

[21] Appl. No.: 467,230

[22] Filed: Jun. 6, 1995

[51] Int. Cl.$^6$ ........................................... G01V 5/12
[52] U.S. Cl. ........................................... 250/269.3
[58] Field of Search ........................ 250/269.3, 258, 250/262, 264, 265, 266

[56] References Cited

U.S. PATENT DOCUMENTS

| | | | |
|---|---|---|---|
| 5,205,167 | 4/1993 | Gartner et al. | 250/269.3 |
| 5,359,195 | 10/1994 | Gartner et al. | 250/269.3 |
| 5,361,632 | 11/1994 | Magnani | 250/258 |

OTHER PUBLICATIONS

Chauvel, et al., "Production Logging in Horizontal Wells: Applications and Experience to Date", *Society of Petroleum Engineers, SPE 21094*, pp. 1–15 (Oct. 1990).

Branagan et al., "Tests Show Production Logging Problems in Horizontal Gas Wells", *Oil & Gas Journal*, pp. 41–45 (Jan. 1994).

Vigneaux, P. G., et al., "Oil/Water Flow Structure Measurements in Inclined Pipes", *Society of Petroleum Engineers SPE 18217*, pp. 383–392 (Oct. 1988).

Hasan, A. R., et al., "A New Model For Two–Phase Oil/Water Flow: Production Log Interpretation & Tubular Calculations", *Society of Petroleum Engineers SPE 18216*, pp. 369–389 (Oct. 1988).

*Primary Examiner*—Carolyn E. Fields

[57] ABSTRACT

A method for determining the downhole flow regime in a horizontal well borehole traversing a subterranean formation. A first gas holdup value within the borehole is measured using a fluid density tool. A second gas holdup value within the borehole is measured using a fullbore gas-holdup tool. The downhole flow regime is then determined as a function of the first gas holdup value and the second gas holdup value. A downhole flow regime comprised of dispersed bubble flow is indicated where the first gas holdup value is approximately equal to the second gas holdup value. A downhole flow regime comprised of annular flow is indicated where the first gas holdup value is substantially greater than the second gas holdup value and the velocity of the gas phase is substantially greater than the liquid phase. A downhole flow regime comprised of stratified flow is indicated where the first gas holdup value is less than or greater than the second gas holdup value.

11 Claims, 2 Drawing Sheets

DETERMINATION OF DOWNHOLE FLOW REGIME IN A HORIZONTAL WELLBORE BY USING CENTER SAMPLE AND FULLBORE GAS-LIQUID HOLDUP MEASUREMENTS

BACKGROUND OF THE INVENTION

1. Field of the Invention

This invention relates to a method of determining the downhole flow regime in a horizontal well borehole. In particular, it relates to a method of determining the downhole flow regime in a horizontal wellbore by use of center sample and fullbore gas-liquid holdup measurements.

2. Description of the Related Art

Production logging (PL) data are used to determine the rate and type of fluid entering or leaving the completion string. The PL data can be classified according to the type of measurement used to obtain the data: fluid velocity, holdup, pressure, temperature, and auxiliary measurements, such as noise. The velocity of the composite downhole flowstream is determined from data obtained from multiple passes of an in-line or fullbore spinner or from data obtained from station measurements made with a diverter/basket flowmeter. The downhole flow rates for each phase are determined from the fluid velocity, the holdup of each phase, and the interphase velocity relationship, which in vertical wells is referred to as the slip velocity. The limitations of fluid-velocity measurements in multiphase flow (e.g., gas, oil, and water) in horizontal wells and in unstabilized flow regimes in vertical wells are well known.

Oxygen-activation measurements from multiple-detector pulsed neutron tools are routinely used for water-velocity determination. Oxygen-activation combined with conventional PL data can be used to determine whether the water movement is inside or outside the production tubulars.

At a particular depth, the holdup of a specified phase (gas, oil, or water) is defined as the fraction of the cross sectional area of the casing or tubing that is occupied by that phase. The traditional holdup logging devices are the radioactive fluid-density (gamma-gamma attenuation), the gradiomanometer (differential pressure), and the water-holdup (capacitance, or dielectric) tools. Differential-pressure holdup measurements must be corrected for well deviation and are unusable in horizontal wells. The radioactive fluid-density and capacitance water-holdup tools are, by design, center-sampling tools and have radial depth of investigation approximately equal to the radius of the logging tool. A center-sampling tool thus measures fluid properties along or near the axis of the tool. An example of a typical center-sampling radioactive fluid-density tool used for gas holdup measurements is a fluid density logging tool, model no. FDT-EC, available from Halliburton Energy Services of Houston, Tex.

The identification of gas entry points in high-angle and horizontal wells is often difficult when high liquid holdups are present. In such situations, the liquid phase occupies a large cross-sectional area of the casing, and the gas, because of its lower density occurs in the upper portion of the casing. At low gas flow rates, the gas phase may occur as individual gas bubbles. As the gas flow rate increases, stratified, or layered, flow can be present. Conventional center-sampling holdup tools cannot identify the gas holdup until the gas occupies an area from the upper surface of the casing downward to near the axis of the centralized logging tool where it is within the radial depth of investigation of the center sample measurement.

In horizontal wells, the type of flow regime may be determined by crossplotting superficial gas velocity against superficial liquid velocity on a flow-pattern map as illustrated in FIG. 1. The various flow regimes in the horizontal well are further illustrated in FIG. 2. The reported surface production rates, converted to downhole volumes and corresponding velocities for the gas and liquid phases, can be entered into the map to obtain the flow regime for 100 percent flow conditions. As discussed earlier, center-sampling holdup tools will give incorrect holdup values in horizontal wells in all multiphase flow regimes except dispersed bubble flow (where the gas phase is uniformly distributed within the liquid phase). Superficial velocity is a function of (1) the total fluid velocity, (2) the slip velocity between the phases, and (3) the phase holdup. Therefore, if incorrect holdup values are utilized, it directly follows that the superficial velocity will also be in error and will thus predict an incorrect flow regime.

Fullbore gas holdup tools are now available which overcome the limitations of the traditional center-sampling tools by providing gas holdup values for the entire wellbore rather than simply the central portion of the wellbore. A gas holdup tool for use in cased well boreholes is disclosed in U.S. Pat. No. 5,359,195, the disclosure of which is incorporated herein by reference. The unique design of the fullbore gas holdup tool disclosed in U.S. Pat. No. 5,359,195 permits the measurement of gas holdup values that represent the entire cross sectional area of the wellbore in which the tool is positioned. The full capability of the fullbore gas holdup tool measurements to date has not been fully developed. In particular, fullbore gas holdup tool measurements have not been used in conjunction with more traditional measurements such as those obtained by the older generation of center sampling gas holdup tools to derive downhole flow regimes.

The present invention is directed to a method for determining the downhole flow-regime that overcomes the limitations of prior methods that relied solely upon center-sampling gas-liquid holdup measurements. In particular, the present invention is directed to a method for determining the downhole flow-regime by utilizing a combination of center sample and fullbore gas holdup measurements.

SUMMARY OF THE INVENTION

In accordance with one aspect of the present invention there is provided a method of determining the downhole flow regime in a horizontal well borehole using center-sampling and fullbore gas-liquid holdup measurements. The gas-holdup is measured at a predetermined position within a horizontal wellbore using both a fluid density tool and a fullbore gas-holdup tool. The gas holdup values are then monitored over time and/or distance (i.e. depth) within the borehole. The measurements are finally correlated to determine the downhole flow regime. Dispersed bubble flow is indicated by a gas holdup measurement obtained from the fluid density tool equal to the gas holdup measurement obtained from the fullbore gas-holdup tool within about plus or minus five percent. Stratified flow is indicated by a gas holdup measurement obtained from the fluid density tool that is more than about five percent less than that obtained from the fullbore gas-holdup tool. Stratified flow is also indicated by a gas holdup measurement obtained from the fluid density tool that is more than about five percent greater than that obtained from the fullbore gas-holdup tool. Stratified wavy flow is indicated by non-uniform or cyclic gas holdup measurements from either the fluid density or fullbore gas holdup tools following a stratified flow regime. Annular flow is indicated by a wavy stratified flow regime followed by a steady-state flow regime in which the gas holdup measurement for the fluid density tool is at least about 75 percent greater than the gas holdup measurement obtained from the fullbore gas-holdup tool.

BRIEF DESCRIPTION OF THE DRAWINGS

The present invention will become more fully understood from the following detailed description of the preferred embodiments, taken in conjunction with the accompanying drawings in which.

DETAILED DESCRIPTION OF PREFERRED EMBODIMENTS

Figure 3:
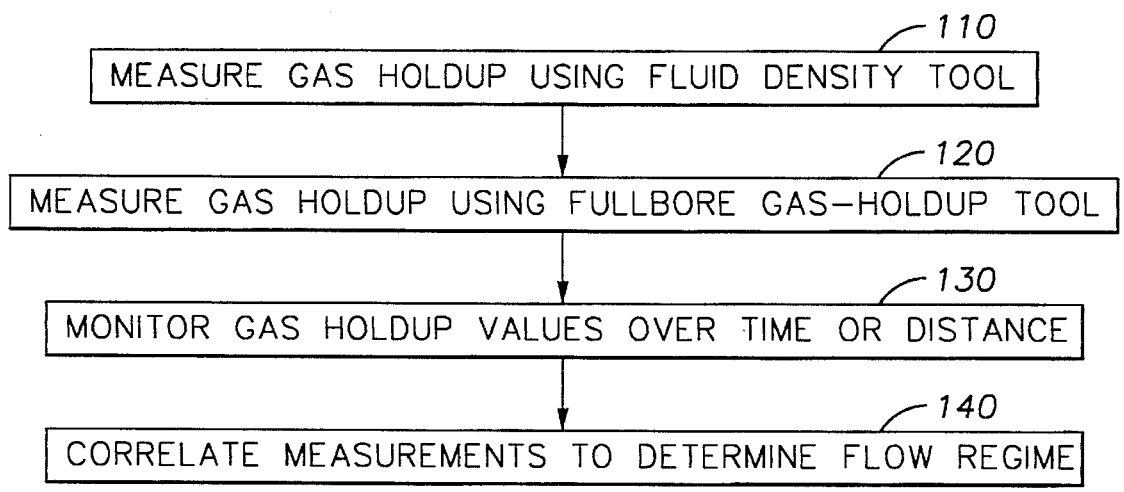
FIG. 3 is a flow diagram of the preferred embodiment of the invention.

Turning now to the drawings, and referring initially to FIG. 3, the preferred embodiment of the present invention utilizes gas holdup measurements obtained from a conventional fluid density tool and also from a conventional fullbore gas-holdup tool to determine the downhole flow regime in a horizontal well borehole. The flow diagram 100 illustrates the steps involved in the preferred embodiment of the present invention. A gas holdup value is obtained at a predetermined position downhole within a horizontal borehole in step 110 using a center-sampling fluid density tool. A horizontal borehole being a borehole inclined at an angle of about 90°±10° relative to the vertical direction. A gas holdup measurement is obtained at the predetermined position downhole within a borehole in step 120 using a fullbore gas-holdup tool. The gas holdup values are then monitored over time and/or distance within the wellbore in step 130. The measurements obtained in steps 110 and 120 are preferably performed simultaneously with the fluid density and fullbore gas holdup tools depth aligned within the well borehole. The monitoring step 130 is performed over sufficient time and/or distance to determine the presence or absence of non-uniform or cyclic flow regimes which are indicated by gas holdup values for either the fluid density or fullbore gas holdup tools which are non-uniform or periodic with variations from the mean value of at least about 10 percent. Finally, the gas holdup measurements are correlated in step 140 to determine the downhole flow regime as discussed below.

Figure 1:
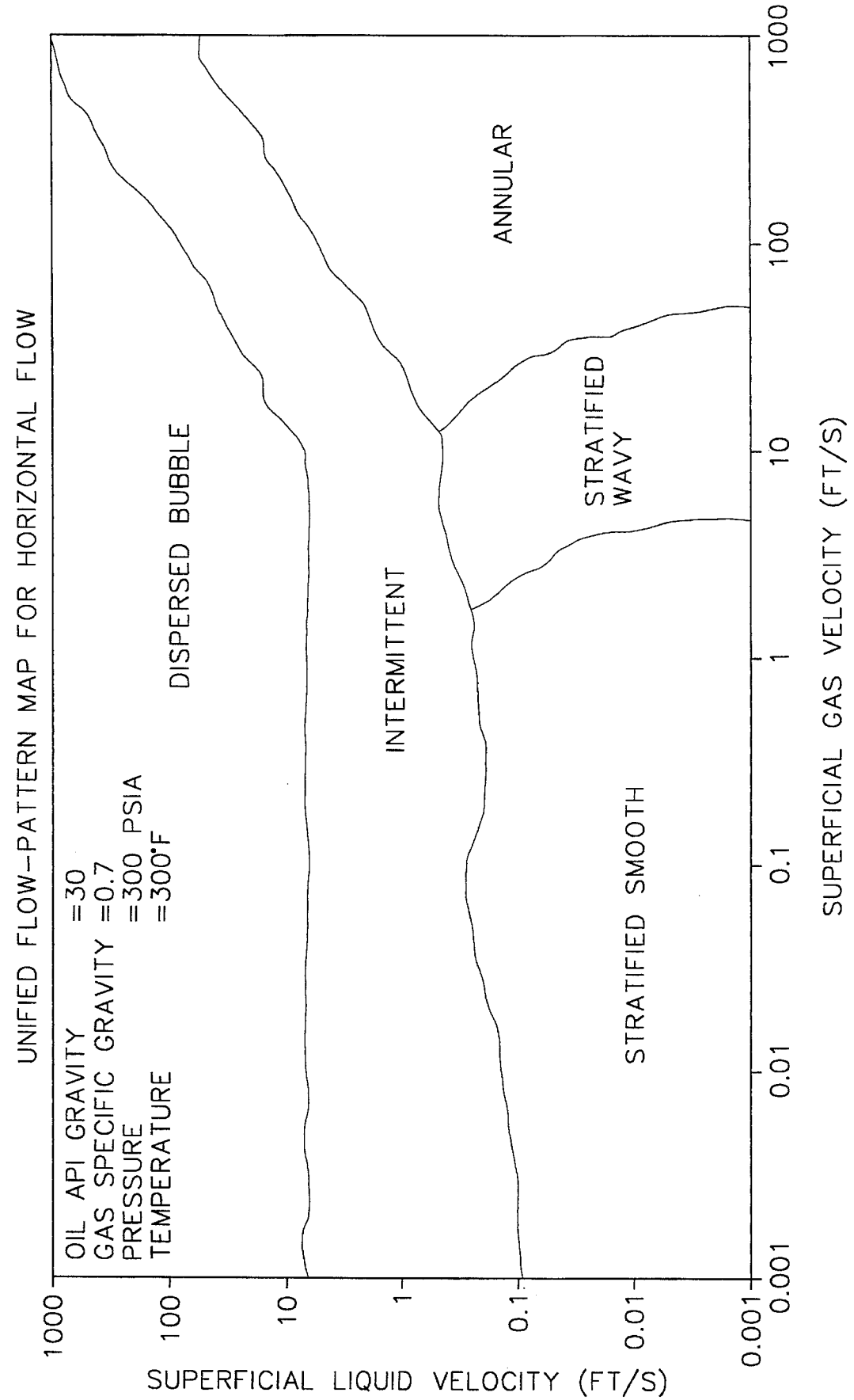
FIG. 1 is a graphical illustration of typical flow regimes in a horizontal wellbore as a function of the superficial gas velocity and superficial liquid velocity.
Figure 2:
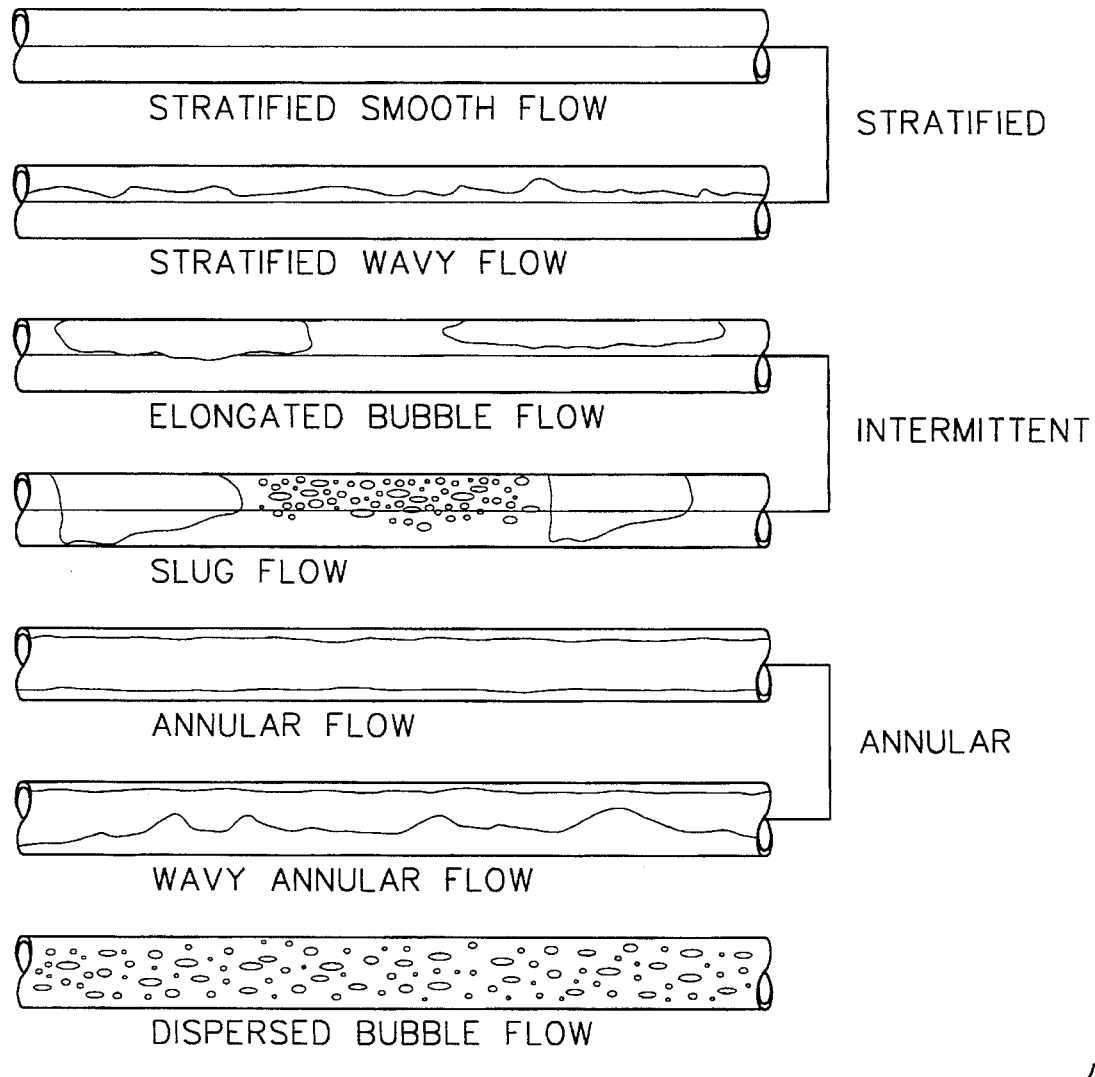
FIG. 2 is a graphical illustration of the various flow regimes illustrated in FIG. 1.

By utilizing the gas holdup values from both the center-sampling fluid-density tool and the fullbore gas-holdup tool, the downhole flow regimes can be determined. This is best illustrated by examining the illustration of flow regimes in FIG. 2 and keeping in mind the measurement capabilities of the two types of logging tools.

Dispersed bubble flow is identified in step 140 when the gas holdup value from the centralized fluid-density tool and the fullbore gas-holdup tool are approximately equal. Since dispersed bubble flow is a flow regime in which the gas holdup is uniform throughout the cross section of the wellbore, both tools should measure approximately the same value for the gas holdup fraction and there should be little variation in the measurement with time. In practice, due to the measurement tolerances of typical centralized fluid-density and fullbore gas-holdup tools, an equal measurement value for the two tools in steps 110 and 120 with a tolerance of about ±5 percent results in a determination in step 130 of dispersed bubble flow.

Stratified flow, with the gas-liquid interface above the center sampling fluid density tool, is identified in step 140 where the gas holdup value for the center sampling fluid density tool indicates no gas phase (all liquid phase) and the gas holdup value for the fullbore gas-holdup tool indicates both gas and liquid phases. Thus stratified flow will be indicated where the gas holdup value for the center sampling fluid density tool is less than the gas holdup value for the fullbore gas holdup tool. This occurs because the gas holdup value for the center sampling fluid density tool indicates no gas phase (or all liquid) for the gas-liquid interface above the center axis of the casing, where the center sampling fluid density tool is positioned, and the fullbore gas holdup tool responds to the full volume of the casing which includes both gas and liquid phases. Due to the measurement tolerances of typical centralized fluid-density and fullbore gas-holdup tools, stratified flow is identified in step 140 where the gas holdup value for the center sampling fluid density tool is more than about 5 percent less than the gas holdup value for the fullbore gas holdup tool.

Stratified flow, with the gas-liquid interface below the center sampling fluid density tool, is identified in step 140 where the gas holdup value for the center sampling fluid density tool indicates all gas phase (no liquid phase) and the gas holdup value for the fullbore gas-holdup tool indicates both gas and liquid phases. Thus stratified flow will be indicated where the gas holdup value for the center sampling fluid density tool is greater than the gas holdup value for the fullbore gas holdup tool. This occurs because the gas holdup value for the center sampling fluid density tool indicates all gas phase (or no liquid) for the gas-liquid interface below the center axis of the casing, where the center sampling fluid density tool is positioned, and the fullbore gas holdup tool responds to the full volume of the casing which includes both gas and liquid phases. Due to the measurement tolerances of typical centralized fluid-density and fullbore gas-holdup tools, stratified flow is identified in step 140 where the gas holdup value for the center sampling fluid density tool is more than about 5 percent more than the gas holdup value for the fullbore gas holdup tool.

Wavy stratified flow is indicated in step 140 when a steady-state stratified flow regime is followed by a non-uniform or cyclic flow regime. A non-uniform or cyclic flow regime is indicated by gas holdup values for the fluid density or fullbore gas holdup tools which are non-uniform or cyclic with variations of at least about 10% from the mean value. The determination of this transitionary flow regime is permitted by monitoring the flow regime within the well borehole over time and/or distance within the well borehole in step 130. Since wavy stratified flow is a transitionary flow regime, its development within the borehole requires time and/or distance within the borehole. The required time and/or distance for the monitoring step 130 will vary as a function of the particular borehole geometry under investigation. In general, a monitoring time ranging from about ½ to 3 minutes and/or a monitoring distance ranging from about 2 to 50 feet will provide sufficient time and distance for the determination of most transitionary flow regimes (i.e., distinguishing them from steady-state flow regimes). The required time and/or distance is a function of the particular geometry of the borehole, the production flow rates, and the fluid properties.

Annular flow is identified in step 140 when a steady-state stratified flow regime is followed by a non-uniform or cyclic flow regime which is then followed by a steady-state flow regime in which the gas holdup value for the fluid density tool is at least about 75 percent greater than the gas holdup value for the fullbore gas-holdup tool. As previously discussed, the non-uniform or cyclic flow regime indicates wavy stratified flow. A steady-state flow regime following the wavy stratified flow regime with the gas holdup value for the fluid density tool at least about 75 percent greater than the gas holdup value for the fullbore gas-holdup tool indicates the presence of annular flow.

Since annular flow is a flow regime in which the center of the wellbore is gas phase and the outer annulus is liquid, the center sampling fluid-density tool gas holdup value will be significantly higher than the gas holdup value for the fullbore gas-holdup tool due to the measurement limitations of the center sampling fluid-density tool. Further, annular flow takes time and/or distance to develop within the well borehole by starting with stratified flow, transitioning to stratified wavy, and then developing into annular. Experimental results using conventional logging tools of both types reveal that a steady-state difference of at least about 75 percent in the gas holdup value following a transition from stratified flow indicates the presence of annular flow.

The correlation of the gas holdup measurements obtained from the fluid density tool and the fullbore gas-holdup tool are summarized in Table 1 below.

TABLE 1

| Flow Regime | Holdup Relationship | Comments |
| --- | --- | --- |
| Dispersed bubble flow | $Y_{g,Fden} = Y_{g,Fullbore}$ | |
| Stratified flow | $Y_{g,Fden} < Y_{g,Fullbore}$ | Gas-liquid interface above fluid-density tool in a horizontal well |
| Stratified flow | $Y_{g,Fden} > Y_{g,Fullbore}$ | Gas-liquid interface below fluid-density tool in a horizontal well |
| Stratified wavy flow | $Y_{g,Fdn} < Y_{g,Fullbore}$ or $Y_{g,Fden} > Y_{g,Fullbore}$ | Non-uniform or cyclic following steady-state stratified flow |
| Annular flow | $Y_{g,Fden} >> Y_{g,Fullbore}$ | Steady-state conditions following transitionary stratified wavy flow |

$Y_{g,Fden}$ represents the gas holdup value determined from the fluid density tool and $Y_{g,Fullbore}$ represents the gas holdup value determined from the fullbore gas-holdup tool.

The determination of the flow regime in step 140 may be performed by a programmed general purpose computer by means of a lookup table, and preferably will also include an accompanying record of the angle of inclination of the logging tools with the gas holdup measurements.

A method has been described for determining the downhole flow regime in a horizontal wellbore by using center sample and fullbore gas holdup measurements that overcomes the limitations and errors introduced into flow regime determinations that rely solely upon the gas holdup value obtained from a conventional fluid density tool.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

What is claimed is:

1. A method for determining the downhole flow regime in a horizontal well borehole traversing a subterranean formation, comprising the steps of:

measuring a first gas holdup value within said borehole using a fluid density tool;

measuring a second gas holdup value within said borehole using a fullbore gas-holdup tool; and determining said downhole flow regime as a function of said first gas holdup value and said second gas holdup value.

2. The method of claim 1, wherein said determined downhole flow regime is dispersed bubble flow for said first gas holdup value approximately equal to said second gas holdup value.

3. The method of claim 2, wherein said determined downhole flow regime is dispersed bubble flow for said first gas holdup value equal to said second gas holdup value to within plus or minus five percent.

4. The method of claim 1, wherein said determined downhole flow regime is stratified flow for said first gas holdup value less than said second gas holdup value.

5. The method of claim 4, wherein said determined downhole flow regime is stratified flow for said first gas holdup value less than said second gas holdup value by more than about five percent.

6. The method of claim 1, wherein said determined downhole flow regime is stratified flow for said first gas holdup value greater than said second gas holdup value.

7. The method of claim 6, wherein said determined downhole flow regime is stratified flow for said first gas holdup value greater than said second gas holdup value by more than about five percent.

8. The method of claim 1, further comprising the step of:

monitoring said first gas holdup value and said second gas holdup values over time;

wherein said determined downhole flow regime is wavy stratified flow for said first gas holdup value or said second gas holdup value being non-uniform or cyclic.

9. The method of claim 8, wherein said determined downhole flow regime is annular flow for said wavy stratified flow regime followed by a steady-state flow regime in which said first gas holdup value is greater than said second gas holdup value by about seventy five percent or more.

10. The method of claim 1, further comprising the step of:

monitoring said first gas holdup value and said second gas holdup values over distance within said borehole;

wherein said determined downhole flow regime is wavy stratified flow for said first gas holdup value or said second gas holdup value being non-uniform or cyclic.

11. The method of claim 10, wherein said determined downhole flow regime is annular flow for said wavy stratified flow regime followed by a steady-state flow regime in which said first gas holdup value is greater than said second gas holdup value by about seventy five percent or more.

\* \* \* \* \*